(12) United States Patent
Edwards

(10) Patent No.: US 7,184,827 B1
(45) Date of Patent: Feb. 27, 2007

(54) SHRINKAGE OF DILATATIONS IN THE BODY

(75) Inventor: Stuart D. Edwards, 658 Westridge Dr., Portola Valley, CA (US) 94028

(73) Assignee: Stuart D. Edwards, Portola Valley, CA (US)

( * ) Notice: Subject to any disclaimer, the term of this patent is extended or adjusted under 35 U.S.C. 154(b) by 0 days.

(21) Appl. No.: 09/490,622

(22) Filed: Jan. 24, 2000

(51) Int. Cl.
*A61N 1/30* (2006.01)

(52) U.S. Cl. .................... 604/21; 604/509; 604/508

(58) Field of Classification Search ............ 604/21, 604/20, 19, 101.05, 103.01, 509, 96.01, 913, 604/95.05, 113, 508; 606/27–29, 31, 32, 606/41–45, 200, 192, 46; 607/122, 101; 623/17.16, 17.12, 23.72, 902, 18.11; 128/898
See application file for complete search history.

(56) References Cited

U.S. PATENT DOCUMENTS

| | | | |
|---|---|---|---|
| 4,587,975 A | | 5/1986 | Salo et al. |
| 4,994,069 A | * | 2/1991 | Ritchart et al. ............ 606/191 |
| 5,423,744 A | | 6/1995 | Gencheff et al. ............ 604/53 |
| 5,500,011 A | | 3/1996 | Desai |
| 5,588,961 A | | 12/1996 | Leone et al. |
| 5,634,899 A | | 6/1997 | Shapland et al. |
| 5,674,287 A | * | 10/1997 | Slepian et al. ............. 128/898 |
| 5,728,066 A | | 3/1998 | Leone et al. |
| 5,779,673 A | | 7/1998 | Roth et al. .................. 604/101 |
| 5,810,763 A | | 9/1998 | Feiring ....................... 604/21 |
| 5,843,156 A | | 12/1998 | Slepian et al. |
| 5,846,218 A | | 12/1998 | Brisken et al. .............. 604/22 |
| 5,865,801 A | | 2/1999 | Houser |
| 5,916,235 A | * | 6/1999 | Guglielmi .................. 606/200 |
| 5,938,660 A | | 8/1999 | Swartz et al. ................ 606/45 |

(Continued)

FOREIGN PATENT DOCUMENTS

WO    WO 85/02779    *    7/1985

*Primary Examiner*—Nicholas D. Lucchesi
*Assistant Examiner*—Melissa A. McCorkle
(74) *Attorney, Agent, or Firm*—Michael A. Glenn; Glenn Patent Group

(57) ABSTRACT

A method and system for shrinking dilatations of a body, removing excess, weak or diseased tissue, and strengthening remaining tissues of the lumen walls. A catheter is disposed near the dilatation and fixed in position by inflatable occlusion balloons. Body fluids present in the occluded dilatation are evacuated and treatment fluid is exuded under pressure into the dilatation. Pressure is maintained by the treatment fluid while energy is applied by the catheter to heat the treatment fluid, causing the lumen walls to absorb the treatment fluid. Additional energy is then applied so as to preferentially heat the lumen wall tissues which have absorbed the treatment fluid, while at the same time treatment fluid is circulated to cool the inner surface of the lumen walls. The dilatation is occluded, a saline solution is introduced and absorbed into the lumen-wall tissue in the occluded region of the dilatation and then heated by application of radio frequency ("RF") or other energy in order to soften only the lumen-wall tissue of the dilatation, the dilatation is shrunk by application of a chilled saline solution and a vacuum, and additional RF or other energy is emitted to ablate, further shrink, and harden only the lumen-wall tissue of the dilatation, without destroying the inner surface of the lumen or other tissues of the body beyond the lumen walls, thereby promoting growth of epithelial cells.

38 Claims, 3 Drawing Sheets

U.S. PATENT DOCUMENTS

| | | | |
|---|---|---|---|
| 5,947,977 A | 9/1999 | Slepian et al. | 606/108 |
| 5,971,983 A * | 10/1999 | Lesh | 606/41 |
| 2002/0156531 A1 * | 10/2002 | Felt et al. | 623/17.16 |
| 2004/0097901 A1 * | 5/2004 | Whalen et al. | 604/509 |

* cited by examiner

213
Additional RF energy may be emitted by the electrodes in the catheter tip assembly 101 at a selected frequency and power level effective to ablate tissues of the lumen walls 105, while chilled treatment fluid 112 is circulated by exuding it in via the ports 111 and suctioning it out via the suction ports 114 in order to minimize heating and damage of cells lining the inner surface of the lumen walls 105 and remove detritus of ablation.

214
The tissues of the lumen walls 105 are hardened in the contracted condition by further application of RF energy and circulation of chilled treatment fluid 112.

215
The occluding balloons 106 and 107 and the treatment balloon 108 are deflated.

216
The catheter 100 is removed from the body of the patient.

220
The dilatation has been treated and should be in a condition for normal operation.

*FIG. 6B*

SHRINKAGE OF DILATATIONS IN THE BODY

BACKGROUND OF THE INVENTION

1. Field of the Invention

This invention relates to techniques for shrinking dilatations in the body by localized tissue modification.

2. Related Art

A dilatation is an abnormally enlarged or distended segment of an otherwise patent biological lumen or conduit, such as the gastrointestinal, genito-urinary, pulmonary, vascular, or other systems in the body. Dilatations may also occur at other places within the body, such as in the nervous system, the eyes, or the skin. The degree of enlargement, the length, and the significance of the dilatation may differ greatly between particular dilatations, and is responsive to the nature of the lumen subject to the dilatation. Various etiological factors might be responsible for the development or exacerbation of any particular dilatation; these may include, for example, blockage, stenosis, infection, inflammation, trauma (whether external, internal, or surgical), or cancer. One or more of these factors causes the affected lumen to enlarge, expand or distend, with consequential compromise of the function of the lumen and increased danger of rupture of the lumen.

Treatment of dilatations is aimed at restoration of normal intraluminal diameter and strengthening of the lumen walls. Because of the presence of abnormal or diseased tissue at the dilatation, surgical treatment by endoscopic or by open surgical techniques often poses extra difficulties and has significant morbidity. Moreover, because the tissue of the lumen wall at the dilatation is already diseased, it often generates further scarring and fibrosis when it heals after surgery, which can lead to recurrence of the dilatation.

Accordingly, it would be advantageous to provide a method and system for treatment of dilatations, such as for example vascular aneurysms, which uses existing tissue, which promotes healing of existing tissue, and which helps to prevent recurrence of the dilatation. This advantage is achieved in an embodiment of the invention whereby the dilatation is occluded, a saline solution is introduced into the occluded region and perfused into the lumen-wall tissue of the occluded region, radio frequency ("RF") or other energy is emitted controllably to heat and soften only the lumen-wall tissue perfused with saline solution in the occluded region of the dilatation, the dilatation is shrunk by application of a chilled saline solution and a vacuum, additional RF or other energy is emitted to ablate, further shrink, and harden only the lumen-wall tissue perfused with saline solution in the occluded region of the dilatation, all without destroying the inner surface of the lumen or other tissues of the body beyond the lumen wall and thereby promoting growth of epithelial cells in the lumen wall.

It would be further advantageous to provide a method and system for treatment of distended, engorged, inflamed or infected tissue such as cysts, gangrenous tissue, necrotic tissue or tumors, including shrinking, reducing, destroying and removing such tissue, from any system of the body including the cardiovascular system, the lymphatic system, the cardiopulmonary system, the gastrointestinal system (head and neck, esophagus, stomach, intestines, colon, rectum), the urogenital system, the nervous system, particular organs such as the kidney or prostate, retinal lesions and skin lesions.

SUMMARY OF THE INVENTION

The invention provides a method and system for treatment of dilatations using a catheter for precise application of RF energy to subsurface lumen-wall tissue to reduce the diameter of an enlarged portion of any sphincter or lumen of the body. The catheter is introduced into a lumen of the body and directed to the vicinity of the dilatation to be treated, the position of the catheter is fixed and the dilatation is occluded between two inflatable balloons, and a first saline solution is introduced into the occluded region at a temperature and pressure sufficient to perfuse the saline solution into tissue of the lumen wall in the occluded region; the first saline solution is then exchanged for a chilled saline solution, a vacuum is applied, and RF energy is emitted at a frequency which is absorbed more readily by the lumen-wall tissue which has absorbed the first saline solution, thereby shrinking, ablating and hardening the lumen-wall tissue of the dilatation without effecting either the mucosal surface of the lumen or other tissues of the body beyond the lumen walls, to modify the lumen to within the range of normal and maintain the normal diameter of the lumen and prevent reformation of the dilatation during a healing period.

DETAILED DESCRIPTION OF THE PREFERRED EMBODIMENT

Figure 1:
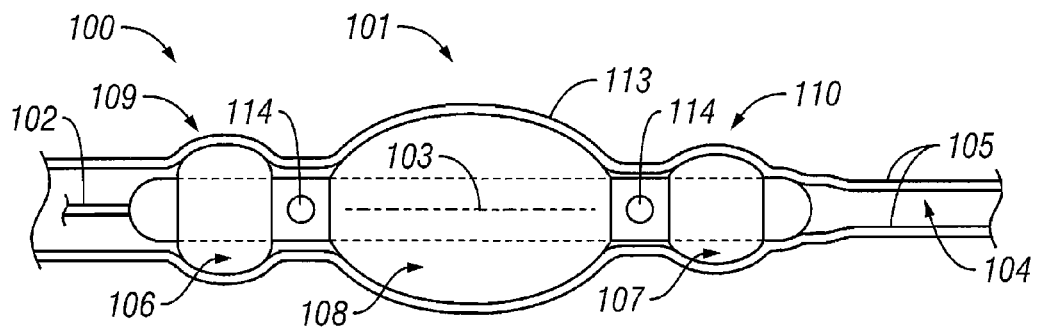
FIG. 1 shows a catheter inserted into a lumen of the body and located in a dilatation of that lumen, with two occluding balloons and an optional intermediate treatment balloon inflated.
Figure 2:
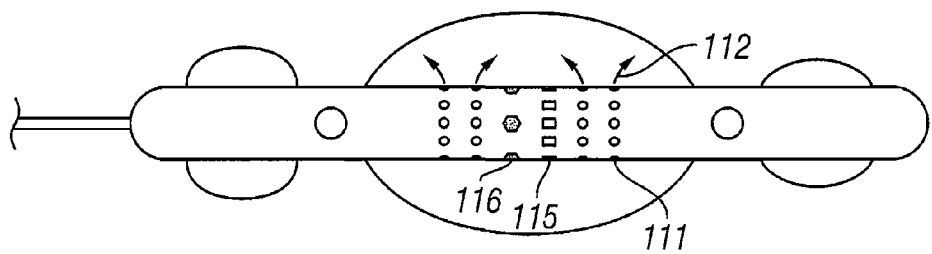
FIG. 2 is a cross-section of the catheter with the sides of the three inflated balloons cut away, showing additional features of the catheter tip assembly.

In the following description, a preferred embodiment of the invention is described with regard to preferred structures and process steps. Those skilled in the art would recognize after perusal of this application that embodiments of the invention can be implemented using structures and process steps adapted for treatment of particular regions of the body, and that implementation of the process steps and structures described herein would not require undue experimentation or further invention.

System Elements

Catheter and Tip Assembly

A catheter 100 includes a tip assembly 101 and a multi-lumen tube 102 coupled thereto. The tip assembly 101 comprises a generally prolate spheroid with a long axis 103. The tip assembly 101 includes a proximal end 109 and a distal end 110, with the proximal end 109 coupled to the multi-lumen tube 102 for coupling control signals, energy and fluids between the tip assembly 101 and a control system (not shown). The tip assembly 101 is disposed in a dilatation 113 of a lumen 104 of the body of a patient with the long axis 103 approximately parallel to lumen walls 105.

In a preferred embodiment, the dilatation 113 in the lumen 104 may comprise an aneurysm in a blood vessel. However, in alternative embodiments, the dilatation 113 may comprise any sphincter or lumen of the body.

In alternative embodiments, the tip assembly 101 may comprise another shape, such as curved or needle-like disposed for fitting within a particular body cavity, for avoiding a particular body structure, or for adaptation to a particular body structure. For example, the tip assembly 11 may comprise a curved, needle-like shape adapted to a surface curvature of an eyeball so that the tip assembly 101 can be inserted under an eyelid.

In a preferred embodiment, the catheter tube 102 comprises a relatively inert and nonconducting substance such as woven dacron. However, in alternative embodiments, the catheter tube 102 may comprise other relatively inert and nonconducting materials such as kevlar, nylon, or plastic, or combinations thereof.

In a preferred embodiment, the tip assembly 101 may include one or more marker elements preferably disposed at or near the distal end 110 of the tip assembly 101 and/or at or near the proximal end 109 of the tip assembly 101, which are noticeable using fluoroscopy or ultrasound or other suitable means. With appropriate x-ray or fluoroscopy equipment, a radiologist or surgeon can position the catheter 100 relative to the dilatation 113 without any requirement for a camera or other optical equipment disposed in or near the dilatation 113. However, in alternative embodiments, such a camera or other optical equipment may be included.

The tip assembly 101 includes at least one port 111, from which a treatment fluid 112 may flow out of the tip assembly 101 and into or near the dilatation 113, and at least one suction port 114. In a preferred embodiment, the port 111 and suction port 114 are further disposed to comprise a fluid circulation system, wherein at least one port 111 is a fluid outlet port and at least one suction port 114 is a fluid inlet port. The fluid circulation system is disposed for circulating fluid in the region of the dilatation 113 near the catheter 100, such as for delivering fluid for cooling the region and for removing other fluid for aspirating the region.

In a preferred embodiment, the port 111 is disposed for delivering substantially equal amounts of treatment fluid 112 in all directions from the tip assembly 101. However, in alternative embodiments, the port 111 may be disposed for delivering differing amounts of treatment fluid 112 in an asymmetrical pattern near the tip assembly 101, either by altering the shape of a single port 111 or by including a plurality of ports 111. For a first example, while in a preferred embodiment there could be a single port 111, alternatively there could be a plurality of ports 111 each substantially the same size but with a variable number of ports 111 located in various locations about the tip assembly 101, and further alternatively there may be ports 111 of substantially different sizes. For a second example, while in a preferred embodiment the ports 111 are each open at all times, in alternative embodiments, they may be subject to a microscopic mechanical device or other technique for closing some or all of them at selected times.

Preferably, the ports 111 are also disposed for removing fluids from the lumen 104. In some embodiments, the ports 111 may handle all fluid delivery and removal during treatment, and no suction ports 114 are needed. All of the ports 111 may be coupled to a single lumen in the catheter tube 102, or some ports 111 may be coupled to one lumen and other ports 111 coupled to another lumen in the catheter tube 102. Preferably, movement of treatment fluid 112 through the ports 111 is controllable so that, according to the needs of a treatment regimen, at a given time all of the ports 111 may deliver treatment fluid 112, all of the ports 111 may remove treatment fluid 112 and/or other fluids, or some ports 111 may deliver treatment fluid 112 while other ports 111 simultaneously remove treatment fluid 112 and/or other fluids.

In an alternative embodiment, separately controllable suction ports 114, coupled to a lumen in the catheter tube 102, may also be located on an exterior surface of the tip assembly 101, and in combination with the ports 111 may comprise a fluid circulation system.

The tip assembly 101 may also include at least one temperature sensor 115 and at least one pressure sensor 116, both preferably disposed at or near the surface of the tip assembly 101. The sensors are coupled using the catheter tube 102 to a control system (not shown) and to an operator presentation device (not shown). The sensors provide signals to the control system for feedback control, and to the operator presentation device for presenting information to an operator.

In a preferred embodiment, the temperature sensor 115 comprises a plurality of temperature sensors, such as thermistors or thermocouples, and the control system provides feed-back control to maintain various temperatures selected by the operator. In a preferred embodiment, the operator presentation device comprises a temperature reporting gauge. However, it would be clear to those skilled in the art that other and further sensor signals, feedback control, and presentation signals would be useful, and are within the scope and spirit of the invention.

In a preferred embodiment, the pressure sensor 116 comprises a plurality of pressure sensors, and the control system provides feedback control to maintain various pressures selected by the operator. In a preferred embodiment, the operator presentation device comprises a pressure reporting gauge. However, it would be clear to those skilled in the art that other and further sensor signals, feedback control, and presentation signals would be useful, and are within the scope and spirit of the invention.

In alternative embodiments, the tip assembly 101 may be fitted with other and further equipment. Such equipment may include a camera or other light-gathering device, either to for aiding a surgeon in manipulating the catheter 100 (e.g., maneuvering the tip assembly 101 to reach the dilatation 113), or for photographically recording the action of the catheter 100 and associated equipment; a laser or other device for ablating or reducing obstructions; or other equipment. Coupling cameras or other light-gathering devices, or lasers or other ablating or reducing devices, to catheters 100 is known in the art of medical devices.

Treatment Fluid

As used herein, the term "treatment fluid" is used generically to mean and refer to any fluid which can act as an electrolyte. In the preferred embodiment, the treatment fluid 112 is a saline solution. However, in alternative embodiments, the treatment fluid 112 may be collagen, a collagenous fluid, or any other fluid which is readily absorbed by the tissue of the lumen walls 104 and which readily absorbs RF energy. In further alternative embodiments, the treatment fluid 112 may comprise medicine, water, or a fluid which is relatively inert and non-bioreactive but heat conductive.

Balloons

The tip assembly 101 also includes a first occluding balloon 106 preferably disposed at or near a proximal end 109 of the tip assembly 101, and a second occluding balloon 107 preferably disposed at or near the distal end 110 of the tip assembly 101. The occluding balloons 106 and 107 are disposed so that when inflated, and in combination with the body of the tip assembly 101, they form a gas-tight or fluid-tight seal against the lumen walls 105 and seal off the portion of the dilatation 113 to be treated from other portions of the lumen 104. The occluding balloons 106 and 107 preferably comprise ring-shaped annular balloons; however, in an alternative embodiment, the distal occluding balloon 107 may comprise a spherical or ellipsoidal balloon disposed at the distal end 110 of the tip assembly 101 in such a manner that when inflated it surrounds the catheter 100 and makes a gas-tight or fluid-tight seal against the lumen walls 104.

In a preferred embodiment, both occluding balloons 106 and 107 are coupled to a single lumen in the catheter tube 102 disposed for delivery of an inflation fluid from a source (not shown). In an alternative embodiment, the occluding balloons 106 and 107 are coupled to separate lumina in the catheter tube 102 disposed for delivery of inflation fluid from sources (not shown), so that the occluding balloons 106 and 107 may be inflated independently of each other.

In a preferred embodiment, at least one occluding balloon 106 or 107 is disposed to anchor the catheter 100 at a selected location within the lumen 104; alternatively, both occluding balloons 106 and 107 may be to anchor the catheter 100. The occluding balloons 106 and 107 when inflated prevent the catheter 100 from being expelled from the body in like manner as the operation of a Foley catheter. However, in alternative embodiments, the balloon used to anchor the catheter 100 may comprise either occluding balloon 106 or 107, or an additional or alternative balloon which is disposed solely or primarily for the purpose of anchoring the catheter 100 into the selected location, again in like manner as the operation of a Foley catheter.

The tip assembly 101 may also include a third balloon 108 (hereinafter referred to as a "treatment balloon 108"), preferably located intermediately between the occluding balloons 106 and 107, which is inflated using a lumen in the catheter tube 102 for delivery of treatment fluid 112 from a source (not shown) through at least one port 111. In a preferred embodiment, the treatment balloon 108 is disposed so that when inflated its surface physically comes into contact with the tissue of the lumen walls 105 which comprise the dilatation 113. The treatment balloon 108 may also include a porous, microporous, or semiporous membrane through which the treatment fluid 112 may flow.

In an embodiment wherein a treatment balloon 108 is used, the suction ports 114 are preferably located between the outside surface of intermediate treatment balloon 108 and the outside surfaces of the occluding balloons 106 and/or 107, so that fluid is drawn into the suction ports 114 from the occluded region of the lumen 104. Preferably, the suction ports 114 may be used either separately or at the same time that treatment fluid 112 is delivered from the ports 111 into the treatment balloon 108.

Electrodes

The catheter 110 also includes at least one electrode, described in more detail below, preferably disposed on the tip assembly 101 between the occluding balloons 106 and 107. The electrodes are coupled using the catheter tube 102 to a power source 120. The power source 120 provides energy to the electrodes, which emit that energy into the lumen walls 105 of the dilatation 113 which have been perfused with the treatment fluid 112 so as to affect the lumen walls 105 of the dilatation 113.

Figure 3:
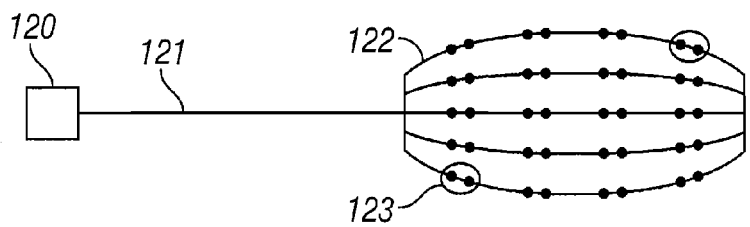
FIG. 3 shows a mesh of direct contact bipolar electrodes that have been expanded by and about the optional intermediate treatment balloon.

FIG. 3 shows a first aspect of the preferred embodiment using direct contact bipolar electrodes 123 to emit RF energy for heating, ablation and/or shrinkage of the dilatation 113. In the first aspect of the preferred embodiment, a plurality of bipolar electrodes 123 are distributed more or less equidistant from each other and disposed so that when the treatment balloon 108 is inflated the electrodes 123 are put in direct contact with the inner surface of the lumen walls 105 in the occluded region of the dilatation 113. In a preferred embodiment, the electrodes 123 are disposed on an expandable conductor mesh 122 surrounding around the treatment balloon 108. In an alternative embodiment, the conductor mesh 122 and electrodes 123 may be disposed in or near the surface of the treatment balloon 108.

Figure 4:
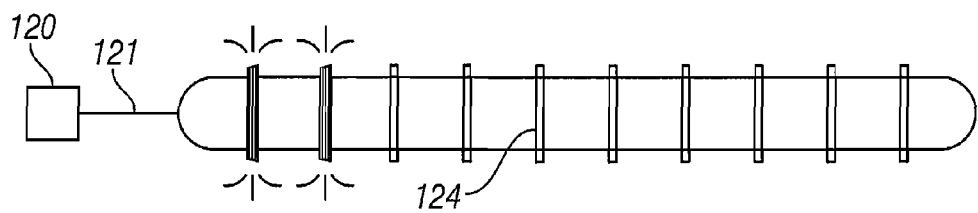
FIG. 4 shows a catheter tip assembly with monopolar ring electrodes that can be used with or without the optional intermediate treatment balloon.

FIG. 4 shows a second aspect of the preferred embodiment using monopolar ring electrodes 124 to emit RF energy for heating, ablation and shrinkage of the dilatation 113. In the second aspect of the preferred embodiment, a plurality of monopolar ring electrodes 124 are disposed repeatedly on or near the surface of the tip assembly 101 between its proximal end 109 and distal end 110.

Figure 5:
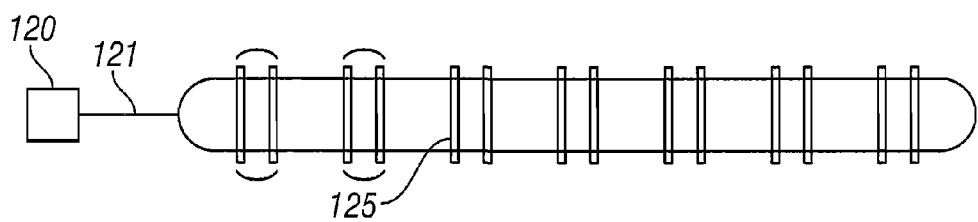
FIG. 5 shows a catheter tip assembly with bipolar ring electrodes that can be used with or without the optional intermediate treatment balloon.

FIG. 5 shows a third aspect of the preferred embodiment using bipolar ring electrodes 125 to emit RF energy for heating, ablation and shrinkage of the dilatation 113. In the third aspect of the preferred embodiment, a plurality of bipolar ring electrodes 125 are disposed repeatedly on or near the surface of the tip assembly 101 between the proximal end 109 and the distal end 110 of the tip assembly 101.

In alternative embodiments, many configurations of electrodes and sensors 116 may operate under processor control to achieve such effects. In a first example, distances between pairs of ring electrodes 124 may be adjusted, either during manufacture, dynamically before use of the catheter tip 101, or otherwise. In a second example, the sensors 116 may be effective to measure other dynamic features of the treatment fluid 112 and lumen-wall tissue of the dilatation 113, such as a localized electrical impedance, a localized fluid flow, or some combination thereof. In a third example, the processor may be effective to control other features of the RF energy, such as a pulse shape or duty cycle of a pulse for RF energy delivery, a frequency for RF energy delivery, a time duration for pulses or time duration between pulses, an order for selection of individual ring electrodes 120 for delivery of RF energy, or some combination thereof.

Energy Source

Electrodes, as described above, are coupled to a power source 120 using a conductor 121 in the catheter tube 102. The conductor 121 is preferably insulated so as to avoid electrical coupling with the catheter tube 102, the treatment fluid 112 or the lumen walls 105. The power source 120 provides energy to the electrodes, which emit that energy into the treatment fluid 112 and tissue of the lumen walls 105 in the occluded region of the dilatation 113.

As used herein, the term "RF energy" is used generically to mean and refer to any means for heating the treatment fluid 112 and/or tissue of the lumen walls 105, broadly including the application of RF energy in a wide range of frequencies, such as the 300 to 700 MHz frequency described herein as well as other microwave frequencies and other frequencies. Those skilled in the art would recognize, after perusal of this application, that other means for heating the treatment fluid 112 and lumen walls 105 may be applied.

For example, where the treatment fluid 112 is a photo-sensitive substance, the means for heating may comprise light. In such an alternative embodiment, the light may be delivered by a laser, light-emitting diode, or other light source coupled to the tip assembly 101.

The energy source 120 is preferably located outside the lumen 104 and outside the body. In a preferred embodiment, the RF energy source 120 generates a continuous or pulsed waveform, preferably a sinusoidal waveform or a square waveform, such as an RF energy generator available as a standard product from Radionics Valley Laboratories, a division of Pfizer, Inc.

In a preferred embodiment, the RF energy source 120 supplies about 50 watts of power, distributed to all of the electrodes 123 collectively, and pulsed in a round-robin fashion among the electrodes 123 so as to equally distribute the delivered energy to all positions along the tip assembly 101.

The RF energy source 120 may comprise a processor which is responsive to signals from the sensors 116 and to a computed or expected amount of the treatment fluid 112 and lumen wall tissue 105 to be treated. The processor computes an effective amount of time and RF energy to deliver to each individual electrode, and controls delivery of RF energy to each individual electrode so as to deliver RF energy to localized points of the treatment fluid 112 and lumen wall tissues 105 which have absorbed it.

Method of Operation

Figure 6A:
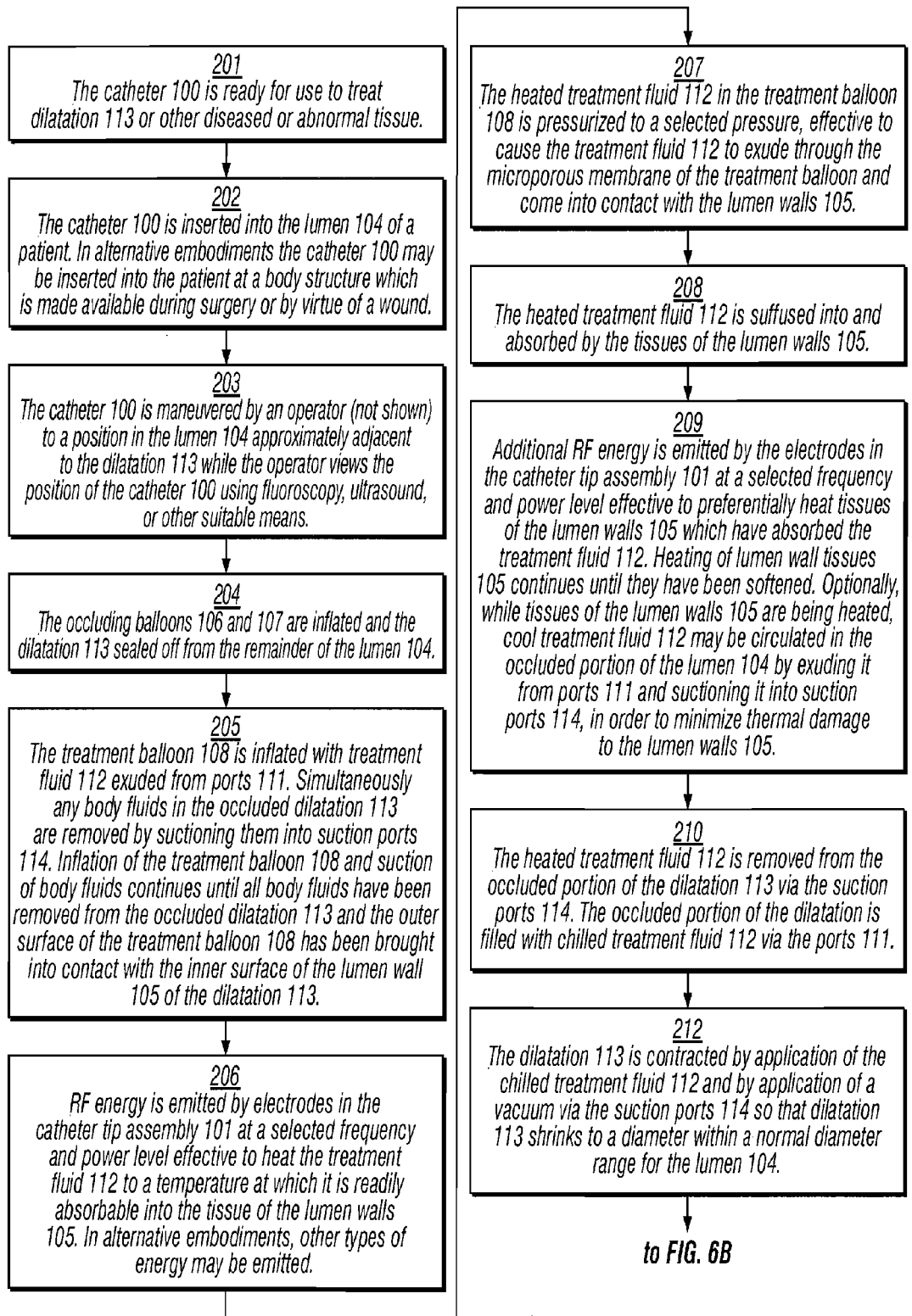
FIG. 6 shows a flow chart of a method of operation for the catheter.

FIG. 6 shows a flowchart for a method of operation of the catheter 100.

A method 200 of operation for the catheter 100 comprises a sequence of steps between the flow points 201 and 220. In the preferred embodiment, the method 200 is carried out using the catheter 100, as well as other and further equipment which would be clearly deemed necessary or desirable by those skilled in the art.

At a flow point 201, the catheter 100 is ready for use to treat dilatation 113.

At a step 202 in a preferred embodiment, the catheter 100 is inserted into the lumen 104 of a patient at a natural body orifice such as the mouth, anus or urethra. However, in alternative embodiments the catheter 100 may be inserted into a blood vessel near a body surface, such as the jugular vein or carotid artery or other blood vessel in the neck, or may be inserted into the patient at a body structure which is made available during surgery or by virtue of a wound; the body structure may comprise a blood vessel, tubular organ, the lymphatic system, a sinus cavity or other ear/nose/throat structure, the intestines, the urethra, a mass of tissue such as a cyst or a fatty deposit, or some other body structure.

At a step 203, the catheter 100 is maneuvered by an operator (not shown) to a position in the lumen 104 approximately adjacent to the dilatation 113 while the operator views the position of the catheter 100 using fluoroscopy, ultrasound, or other suitable means.

At a step 204, the occluding balloons 106 and 107 are inflated and the dilatation 113 sealed off from the remainder of the lumen 104.

At a step 205, the treatment balloon 108 is inflated with treatment fluid 112 exuded from ports 111 while simultaneously any body fluids in the occluded dilatation 113 are removed by suctioning them into suction ports 114 disposed on the tip assembly 101 between the occluding balloons 106 and 107 and coupled to a suction lumen in the catheter tube 102. Body fluids are thus removed from the occluded portion of the dilatation 113 by the dual action of suction outside the treatment balloon 108 and pressure within it. Inflation of the treatment balloon 108 and suction of body fluids continues until all body fluids have been removed from the occluded dilatation 113 and the outer surface of the treatment balloon 108 has been brought into contact with the inner surface of the lumen wall 105 of the dilatation 113.

At a step 206, RF energy is emitted by electrodes in the catheter tip assembly 101 at a selected frequency and power level effective to heat the treatment fluid 112 to a temperature at which it is readily absorbable into the tissue of the lumen walls 105.

At a step 207, the treatment fluid 112 in the treatment balloon 108 is pressurized to a selected pressure, effective to cause the treatment fluid 112 to exude through the microporous membrane of the treatment balloon and come into contact with the lumen walls 105.

At a step 208, the heated treatment fluid 112 is suffused into and absorbed by the tissues of the lumen walls 105.

At a step 209, additional RF energy is emitted by the electrodes in the catheter tip assembly 101 at a selected frequency and power level effective to preferentially heat tissues of the lumen walls 105 which have absorbed the treatment fluid 112. Optionally, while tissues of the lumen walls 105 are being heated, cool treatment fluid 112 may be circulated in the occluded portion of the lumen 104 by exuding it from ports 111 and suctioning it into suction ports 114, in order to minimize heating and damage of cells lining the inner surface of the lumen walls 105. Heating of lumen wall tissues 105 continues until they have been softened.

At a step 210, the heated treatment fluid 112 is removed from the occluded portion of the dilatation 113 via the suction ports 114 and the occluded portion of the dilatation is filled with chilled treatment fluid 112 via the ports 111.

At a step 212, the dilatation 113 is contracted by application of the chilled treatment fluid 112 and by application of a vacuum via the suction ports 114 so that dilatation 113 shrinks to a diameter within a normal diameter range for the lumen 104.

At a step 213, additional RF energy may be emitted by the electrodes in the catheter tip assembly 101 at a selected frequency and power level effective to ablate tissues of the lumen walls 105, while chilled treatment fluid 112 is circulated by exuding it in via the ports 111 and suctioning it out via the suction ports 114 in order to minimize heating and damage of cells lining the inner surface of the lumen walls 105 and remove detritus of ablation.

At a step 214, the tissues of the lumen walls 105 are hardened in the contracted condition by further application of RF energy and circulation of chilled treatment fluid 112.

At a step 215, the occluding balloons 106 and 107 and the treatment balloon 108 are deflated.

At a step 216, the catheter 100 is removed from the body of the patient.

At a flow point 220, the dilatation has been treated and should be in a condition for normal operation.

ALTERNATIVE EMBODIMENTS

Although preferred embodiments are disclosed herein, many variations are possible which remain within the concept, scope, and spirit of the invention, and these variations would become clear to those skilled in the art after perusal of this application.

The invention claimed is:

1. A method for treating a dilatation of a body, including the steps of:
inserting a catheter into a localized region of said body;
exuding from said catheter a substance capable of perfusing into at least some tissue in said localized region and allowing said substance to perfuse into a tissue of said localized region;
emitting from said catheter energy of a frequency and in an amount effective to heat the substance to a temperature at which it is readily absorbed into a wall of said dilatation;
softening tissue of a wall of said dilatation by application of additional energy at a frequency and power level effective to preferentially heat said tissue of said walls while minimizing thermal injury to an inner surface of said dilatation; and
permanently contracting said dilatation by applying a vacuum by means of at least one suction port so that the dilatation shrinks to a desired diameter.

2. A method as in claim 1, wherein said localized region Includes a lumen or sphincter.

3. A method as in claim 1, wherein said localized region includes cancerous, engorged, inflamed or infected tissue.

4. A method as in claim 1, wherein said localized region includes an aneurysm, a blocked lumen, a stenosed lumen or a constricted lumen.

5. A method as in claim 1, wherein said localized region includes a cyst, tumor or wart.

6. A method as in claim 1, wherein said localized region is associated with a body system, said body system including a blood vessel, lung tube, lung pocket, gastrointestinal system, urogenital system, nerve or nerve sheath.

7. A method as In claim 1, wherein said localized region is associated with a particular organ Including a kidney, prostate, retinal lesion or skin lesion.

8. A method as in claim 1, wherein said exuded substance includes a saline solution.

9. A method as in claim 1, wherein said exuded substance includes a non-toxic foam.

10. A method as in claim 1, wherein said exuded substance includes a collagen.

11. A method as in claim 1, wherein said exuded substance includes a bioactive substance, said substance including a drug or enzyme.

12. A method as in claim 1, wherein said exuded substance includes a chemoactive substance including an acid, lipid-breaker or soap.

13. A method as in claim 1, wherein said exuded substance includes an instrumentative substance including a florescent or x-ray marker.

14. A method as in claim 1, wherein said energy is emitted by electrical contact.

15. A method as in claim 1, wherein said emitted energy includes RF (monopolar or bipolar), microwave or laser.

16. A method as in claim 1, wherein said emitted energy includes ultrasound.

17. A method as in claim 1, wherein said emitted energy includes physical heating or cooling.

18. A method as in claim 2, wherein treatment includes shrinkage of said lumen or said sphincter to a selected dimension.

19. A method as In claim 2, wherein treatment includes shrinkage of said lumen or said sphincter to a substantially normal dimension.

20. A method as in claim 1, wherein treatment includes shrinkage of said engorged or inflamed tissue by removal of lipids or water.

21. A method as in claim 1, wherein treatment includes shrinkage of said engorged or inflamed tissue by removal of an ablated tissue or a dead cell matter.

22. A method as in claim 1, wherein treatment includes shrinkage of said engorged or inflamed tissue by removal of infection products.

23. A method as in claim 1, wherein treatment includes destruction of a damaged or a diseased tissue.

24. A method as in claim 1, wherein treatment includes promotion of epithelial growth.

25. A method as in claim 1, wherein treatment avoids local nerve centers.

26. A method as in claim 1, including an additional step of isolating said localized region using a structure inserted as part of said catheter.

27. A method as in claim 26, wherein said inserted structure includes an occluding balloon.

28. A method as in claim 26, wherein said inserted structure includes a space-filling balloon with a lumen through it.

29. A method as in claim 1, wherein said catheter includes instrumentation used for feedback.

30. A method as in claim 29, wherein said feedback includes surgical visualization provided by a camera, RF energy, x-rays, florescence or ultrasound.

31. A method as in claim 29, wherein said feedback includes systemic feedback, comprising measurement of pH, pressure or temperature.

32. A method as in claim 29, wherein said feedback includes monitoring for said treatment, including an element for determining a location of a specified tissue element to be treated.

33. A method as in claim 29, wherein said feedback includes monitoring for said treatment, including pacing.

34. A method as In claim 1, wherein said exuding and perfusing includes a physical method of delivery.

35. A method as in claim 34, wherein said exuded and perfused substance includes a saline solution or nontoxic foam.

36. A method as In claim 34, wherein said physical method of delivery includes a porous balloon, a microporous balloon, or a balloon with a porous or microporous membrane.

37. A method as in claim 34, wherein said physical method of delivery includes direct emission from said catheter.

38. A method as in claim 34, wherein said physical method of delivery includes a local structure, comprising an absorbable basket or a stent.

* * * * *